Figure 1:
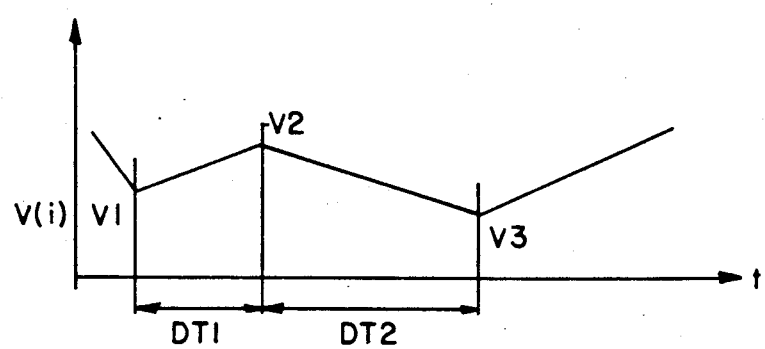

United States Patent [19]

Kanerva et al.

[11] Patent Number: 5,033,070
[45] Date of Patent: Jul. 16, 1991

[54] METHOD FOR PRODUCING A CONTINUOUS PANORAMIC RADIOGRAPH IN A SET OF SEPARATE EXPOSURE SEQUENCES

[75] Inventors: Heikki K. J. Kanerva; Erkki H. Tammisalo; Pasi T. Mustalahti, all of Turku; Olli J. Ojala, Piikkiö, all of Finland

[73] Assignee: Orion-Yhtyma Oy, Helsinki, Finland

[21] Appl. No.: 462,818

[22] Filed: Jan. 9, 1990

[30] Foreign Application Priority Data

Jan. 19, 1989 [FI] Finland .................................. 890294

[51] Int. Cl.$^5$ ........................ A61B 6/14; G03B 42/04; G03B 42/02
[52] U.S. Cl. ........................................ 378/39; 378/38; 378/40; 378/170; 378/175; 378/191; 378/168
[58] Field of Search ..................... 378/40, 39, 38, 170, 378/175, 191, 168

[56] References Cited

U.S. PATENT DOCUMENTS 4,783,793 11/1988 Virta et al. ............................ 378/40

Primary Examiner—Edward P. Westin
Assistant Examiner—Don Wong
Attorney, Agent, or Firm—Bucknam and Archer

[57] ABSTRACT

A panoramic method for the radiography of the dental arch and jaws, in which method by means of movable radiographing and/or imaged elements, several subsequent exposure sweep sequences are performed so that the moving elements are transferred to a new position betwen the subsequent exposure sequences. In order to achieve a perfectly jointed X-ray picture, the movement of the moving elements is started before the switch-on instant of the X-ray beam in the latter exposure sequence and the starting positions of said elements is selected so as to obtain desired positions and velocities for the elements at the switch-on instant of the X-ray beam. The coincidence of the X-ray beam orientation at the start of the latter exposure sequence with the X-ray beam orientation at the end of the preceding sequence is characterizing to an embodiment of the invention.

7 Claims, 2 Drawing Sheets

METHOD FOR PRODUCING A CONTINUOUS PANORAMIC RADIOGRAPH IN A SET OF SEPARATE EXPOSURE SEQUENCES

The present invention relates to a panoramic method for the radiography of the dental arch and jaws, in which method by means of movable radiographing and/or imaged elements, several subsequent exposure sweep sequences are performed so that the X-ray beam and the exposure movement of the moving elements are switched off at the end of a preceding sequence, the moving elements are transferred to a new position and the exposure movement for a latter sequence is started and the X-ray beam is switched on.

The panoramic radiography of the areas of the dental arch and jaws is conventionally performed by orbiting the X-ray source and X-ray film with the help of the so-called support arm about the object to be radiographed placed between them. The X-ray film is moved during the rotation and its movement is generally synchronized with the rotational movement. Furthermore, the pivotal axis of the X-ray beam can be arranged to be movable.

The panoramic radiography can be carried out as a continuous exposure or, alternatively, it consists of a set of separate exposure sequences. Among other things, a disadvantage of the conventional continuous radiograph is that the requirement of continuity in the exposure prevents an individual optimization of the projection geometry for each area to be radiographed. A compromise results therein between the orthogonality of the projections so essential to the image quality and the distance of the X-ray beam.

A panoramic method based on split image exposure sequences (refer to, e.g., U.S. Pat. No. 4,251,730) uses consistently a long distance of the exposing X-ray beam, thereby achieving a good projection at the molar and premolar areas and facilitating the bypass of the cervical spine without a major change in the exposure angle. The disadvantage of this method, however, is a discontinuity of the panoramic radiograph at the frontal area of the dental arch. According to the FI patent application FI 834885, the distance of the X-ray beam can be made larger by retarding the transversal movement, or the x-movement, of the patient chair at the frontal area of the dental arch, whereby the imaged layer will be thicker. This, however, leads to the thinning of the imaged layer at the molar area, where, on the contrary, the imaged layer should be thick, since different individuals may show wide variations in the shape of the dental arch and inclination of teeth also at the molar area.

Shortly, it can be farily stated that so far it has been impossible to produce a continuous panoramic radiograph capable of presenting the jaws and dental arch in a gapless, continuous radiograph with a projection geometry and thickness of the imaged layer meeting the requirements set for a high-quality radiograph.

Therefore, the object of the invention is to provide a method for producing a continuous high-quality panoramic radiograph from a set of separate exposure sequences. The method providers for combining the partial images into such a continuous panoramic radiograph in which it is impossible by visual inspection to detect its formation from separate exposure sequences. This condition is fulfilled only when the procedure for the separate exposure sequences conforms to the following:

the film continues its movement during the latter exposure sequence from the position it was at the end of the preceding sequence, the X-ray beam continues its exposure movement in the latter sequence from the same position relative to the patient where the preceding sequence was terminated, alteration in the X-ray beam distance is allowed between two subsequent exposure sequences only when the foregoing conditions are fulfilled, and the projection angle is allowed to change between two subsequent exposure sequences only when the foregoing conditions are fulfilled.

In addition to the conditions stated above for the combination of static partial images in the panoramic radiography, the elements moving during the exposure must have velocities compatible with a predetermined program. Therefore, the moving elements must have predetermined positions with predetermined speeds at the start and end of each exposure sequence. Thus, the object of the invention is to arrange intermediate parking of these moving elements so that the position and speed conditions for each element are fulfilled at the start of the latter exposure sequence.

The invention achieves the solution of the above stated conditions in such a way, and the invention is characterized in that a corrective movement is incorporated into the transfer movements of the moving elements so that the new start position of the latter sequence is positioned earlier relative to the position corresponding to the actual switch-on position of the X-ray beam in the latter sequence and that the moving elements are brought into motion prior to the switch-on instant of the X-ray beam so that desired positions and speeds for the elements moving at the switch-on instant are attained.

Consequently, the implementation in accordance with the invention is based on the fact that the different elements of the exposure system do not stop immediately after the X-ray is switched off, but instead continue their movements inertially for some time. If the moving parts were transferred only by the amount required by the difference between the direction prevailing at the switch-off instant of the X-ray beam at the end of the preceding sequence and the direction appropriate for the switch-on instant of the X-ray beam at the start of the latter sequence, the shift caused by the inertial movements would result in the exposure of an incorrect area as well as erroneous direction of the X-ray beam. This is the phenomenon which causes the undesirable discontinuities in panoramic radiography.

Secondly, the simultaneous switch-on of the X-ray beam with the simultaneously initiated starting of the moving parts at the start of the latter sequence would result in an exposure by the X-ray beam while the moving parts were still stationary or moving at an incorrect speed. In order to fulfill the positional and speed conditions, the transfer coordinates must be corrected prior to the start of the latter sequence so that the correction is in the opposite direction to that of the latter sequence and with such amount that the moving parts can be accelerated to a desired speed, and at that speed pass a desired point at which the X-ray beam is then switched on.

In a preferred embodiment of the invention, the panoramic radiography is carried out by combining the consecutive exposure sequences so that a continuous radiograph is formed. Herein the transfer movement is carried out so that the exposure in the latter sequence is started at the imaged area and the position of the X-ray film where the preceding sequence was stopped. In this method the distance of the exposing X-ray beam and the projection angle of the image can make a shift during the subsequent exposure sequences. The shift of the projection angle can be performed advantageously in order to, for instance, bypass the cervical spine or radiograph the area of the mandibular joints. The required shift is then from 10° to 30°, preferredly approx. 20°.

In order to achieve a better controllability of the X-ray beam, the transfer movement of the moving parts such as the X-ray source or X-ray film is advantageously performed so that the direction of the X-ray beam at the start of the latter sequence is coincident with the direction of the X-ray beam at the end of the preceding sequence. This arrangement allows linear translations along the axis of the X-ray beam without rotation of the beam.

The description above dealt with the moving, exposing and/or imaged elements. The detailed assignment of the elements is not essential for the implementation of the invention. The moving elements can thus be, e.g.: the X-ray source, the recording element of the radiographic image such as an X-ray film with its cassette, as well as the element used for orbiting the X-ray source and the recording element about the object placed between them for radiographic imaging such as the support arm carrying the X-ray source at one end and the X-ray film with cassette at the opposite end. Alternatively the moving element can be the element used for transferring said support arm along the anterior-posterior axis (y-movement) relative to the patient, along the transverse axis (x-movement) relative to the patient, as well as both along the anterior-posterior and the transverse axes (y- and x-movements). In addition to other movements, other moving elements are feasible as well. Furthermore, the different types of movements can be performed both during as well as in between the exposure sequences. The essential, however, is that the corrected combination of exposure sequences is performed in accordance with the invention.

Moreover, the radiographed object as such or in combination with the moving elements of the radiography system can act as the moving element in accordance with the invention. Thence, the method disclosed in FI patent application 834885 can be applied so that the corrected combination of the different exposure sequences is performed in accordance with the present invention.

In the construction of an apparatus capable of implementing the method in accordance with the invention, it is required that the speed of each moving element can be freely controlled and that the X-ray beam can be switched on and off at desired instants. A mechanically interconnected system capable of achieving the desired speed profiles is conceivable. In current technology, however, the use of stepper motors and microprocessor-controlled movements may be the only reasonable approach to implement such a system. In fact the exact corrections of the movements in accordance with the invention have become possible in practice only through microprocessor-controlled technology.

In the following, the invention is described in greater detail with references to the attached drawings and description of the algorithm preferredly used in the method.

Figure 2:
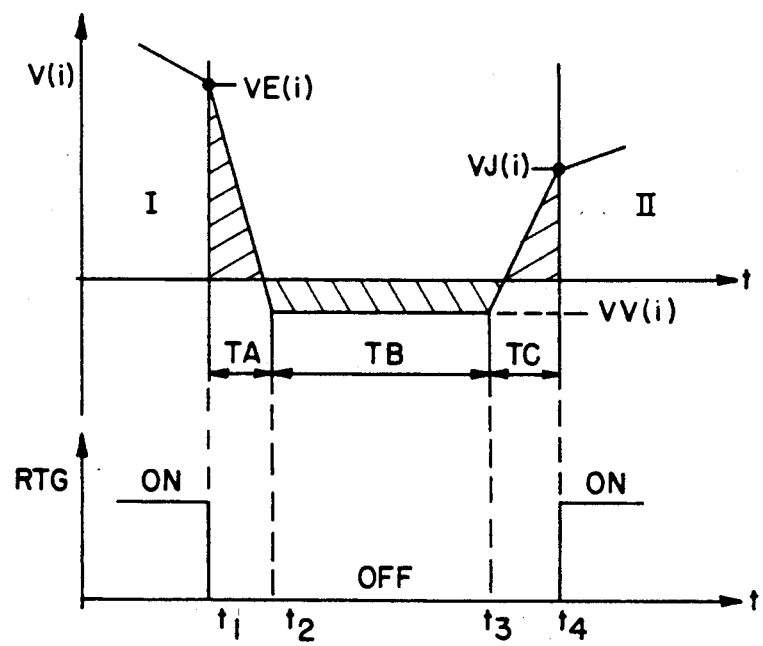
Figure 3:
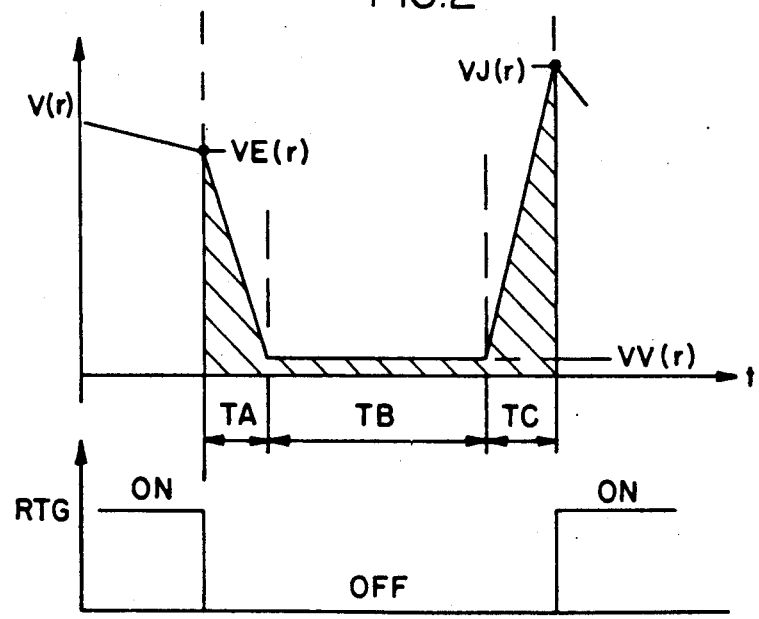
Figure 4:
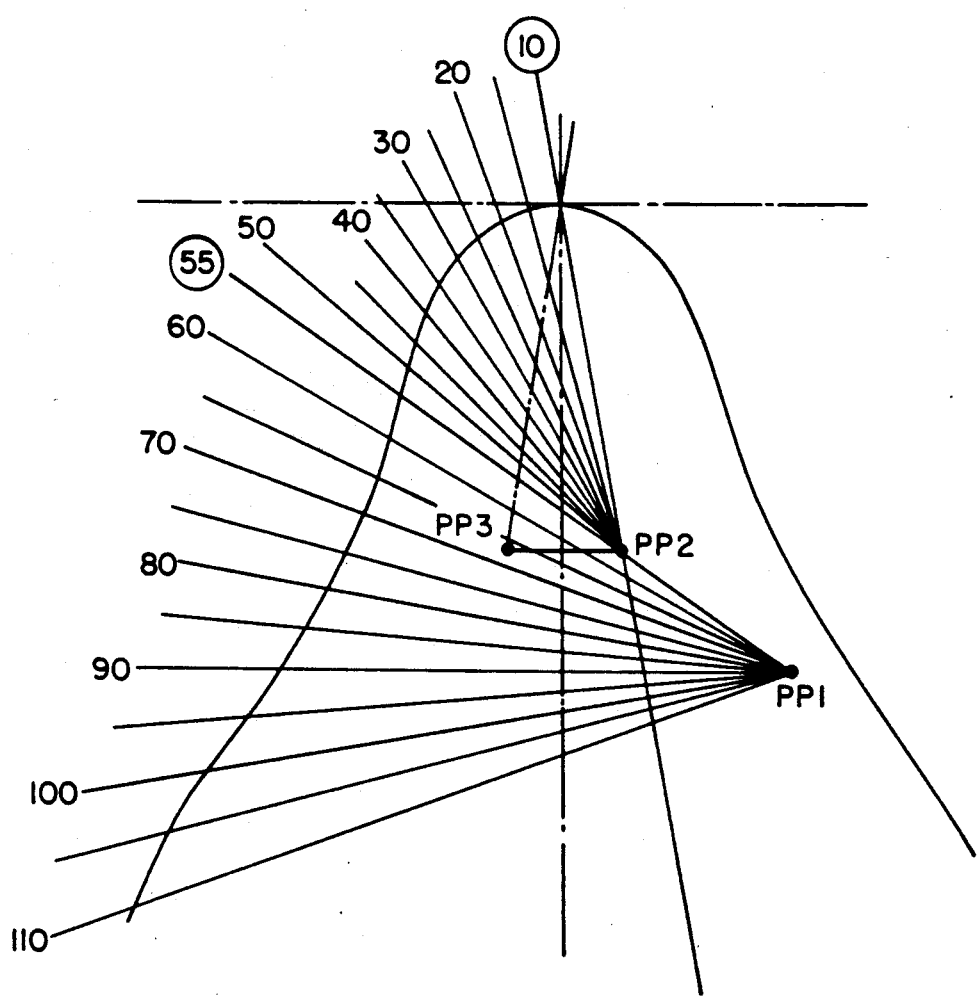

FIG. 1 shows the speed of the moving element as a function of time,

FIG. 2 shows the speed of the moving element as a function of time when the correction of the transfer movement alone, or the correction transfer, is performed, FIG. 3 shows the speed of the moving element as a function of time when both the correction transfer and the projection geometry alteration transfer are performed, and FIG. 4 shows diagrammatically an embodiment of panoramic radiography in accordance with the invention using 3 exposure sequence joints.

Illustrated in FIG. 1 is the speed of a moving element i as a function of time with several values of variables entered to the processor such as: speed values V1, V2, V3, etc., together with time interval values DT1, DT2, etc. The processor then uses the tabulated array of transfer movements so that during time interval DT1 the speed changes from value V1 to value V2, during time interval DT2 from V2 to V3, etc. In this manner a desired speed profile can be implemented as a polyline function. An additional presumption herein is that each moving element adheres to the same interval sequence, moreover, with identical timing which means that the inflection points of the polyline function are coincident for each moving element.

The described control principle is definitely not the only feasible, yet it is good, economical and well suited for practical purposes. Within the scope of the invention several other speed control systems are equally possible as long as they can implement at least two subsequent radiographic expdsdre sweep sequences.

Illustrated in FIG. 2 is the timing diagram for the velocity profile of moving element such as the cassette vs. the X-ray beam switch-on. The velocity $V(i)$ of the moving element is shown as a function of time. The corrective transfer, or intermediate parking, between the exposure sequences takes place during time intervals TA, TB, TC, while the X-ray beam is not switched on. Because this embodiment aims to achieving a picture corresponding to a continuous panoramic radiograph by eliminating any visible joints of consecutive exposure sequences on the film, the net length of film travel during the intermediate parking must be 0; therefore, the hatched areas above and below the t-axis must cancel each other.

Shown in FIG. 2 is how at the end of the exposure sequence the cassette movement is retarded, reversed, returned for a new acceleration, again reversed, accelerated, and thus at the start of the latter exposure sequence, the cassette is exactly in the same position as at the end of the preceding sequence and has an appropriate velocity for the latter exposure sequence.

An intermediate parking is performed between exposure phases I and II as illustrated in FIG. 2 by the obliquely hatched areas. The X-ray beam is switched off at instant $t_1$ and switched on again at instant $t_4$. At the end of the exposure phase I the velocity of the moving element is $VE(i)$, while the velocity at the start of exposure phase II must be $VJ(i)$. An additional condition is that the moving element must perform a translation $DP(i)$ during the intermediate parking.

The velocity of the moving element changes in the intermediate parking during the time interval TA from value $VE(i)$ to value $VV(i)$. The element is moved with the velocity of the corrective movement, or parking velocity, $VV(i)$ for a duration TB, after which the velocity is changed during time interval TC to the desired velocity VJ(i) of the exposure sequence. Solving the equation of hatched areas obtains $$DP(i) = [VE(i) + VV(i)] \cdot \frac{TA}{2} + VV(i) \cdot TB + [VV(i) + VJ(i)] \cdot \frac{TC}{2}$$

The equation can be solved for the velocity VV(i) required for the corrective movement of each moving element. In the diagram the corrective velocity VV(i), or intermediate parking velocity, is shown with an opposite sign to that of the exposure velocities VE(i) and VJ(i). This is the case in practice if, for instance, the requirement DP(i) =0 is set (corresponding to intermediate parking of film and rotation at an unchanged projection angle). The essential in image jointing, however, is that the following jointing conditions for intermediate parking are fulfilled for each moving element:
the terminal velocities correspond to the initial start and end velocities of the exposure phases,
the translation of the moving element corresponds to the requirement set by the projection geometry.

Illustrated in FIG. 3 is the situation in which a discontinuous angular translation is performed in the intermediate parking of the rotational movement. Such a situation is present in a discontinuous transfer to a new object to be exposed or a change of projection angle for the same object. In this case the net translation of intermediate parking is different from zero. Shown in the figure is a positive value of intermediate parking velocity VV(r), but the velocity can equally well be positive or negative, depending on the magnitudes of translations, time intervals and velocities. For this case as well, the equation written for FIG. 2 remains valid.

In practice, constant values for the ramping intervals TA and TC can be selected. The interval TB of exposure movement is selected case-by-case avoiding overload to any moving element. The transfer velocities VV, or intermediate parking velocities, are determined for each element according to the desired translation during the intermediate parking.

Illustrated in FIG. 4 is a panoramio radiography method in accordance with an embodiment of the invention, in which the transfer movement so that the orientation of the X-ray beam at the start of the latter sequence is coincident with orientation angle 55 of the X-ray beam at the end of the preceding sequence. The projection center of panoramic radiography can initially be located at, for instance, point PP1 and the direction of the X-ray beam oriented to angle 110. The first exposure sequence is stopped at orientation angle 55 of the X-ray beam, after which the center of rotation is transferred from the point PP1 to the point PP2. While the center of rotation is at the point PP1, the translation movement is implemented by performing a corrective movement in accordance with the invention that is opposite in direction to the movement so far performed in the preceding exposure sequence and equal in magnitude to the translation caused by inertial forces after the switch-off of the X-ray beam or of the exposure movement. After the corrective movement the direction of the X-ray beam will be exactly identical to that at the switch-off instant of the X-ray beam. A similar correction can be performed for the X-ray film in the cassette so that the inertial translation after the switch-off instant is corrected by an opposite movement of corresponding magnitude, thereby achieving the return of the film in the cassette exactly to the same location it was at the switch-off instant of the X-ray beam.

Next, the center of rotation can be moved from the point PP1 to the point PP2 along the orientation angle 55 of the X-ray beam. The subsequent transfer to be performed is in the opposite direction to the former radiographic exposure movement and with such a magnitude that allows the acceleration of the moving elements, i.e., the X-ray source and the film in the cassette, to a desired velocity for the latter exposure sequence covering orientation angles 55-10 before the X-ray beam is switched on. Finally, the X-ray beam and the exposure movement of the moving elements are activated and the latter radiographic exposure sequence is carried out up to direction angle 10 of the X-ray beam.

The bypass of, for instance, the cervical spine is performed by transferring the center of rotation in the transversal direction, or the x-direction, from the point PP2 to the point PP3 so that the orientation of the X-ray beam toward the object is retained, while altering the projection angle by 20 degrees. In addition, the implementation of this transfer is achieved by means of corrective actions in accordance with the invention.

Finally, a similar exposure sweep to that performed earlier from the point PP2 is carried out from the point PP3. The transfer to the point PP4 (not shown) takes place in a similar manner as the above described change from the point PP1 to the point PP2.

The present invention makes it possible to achieve a picture corresponding to a continuous panoramic radiographic image notwithstanding the fact that the picture is formed through several exposure sequences, the additional benefits being a projection distance of about twice that possible in the conventional methods of continuous radiography known in the art, and moreover, without resorting to impairments in the requirement for orthogonality. The invention is thereby capable of overcoming the most serious present disadvantage, which is the blurred imaging of frontal area of the dental arch. In addition, bypass of the cervical spine is possible, making it possible to avoid the nuisance of shadowing by the cervical spine onto the frontal area of the dental arch.

With the help of the invention it is also possible to alter both horizontal and vertical projections within the exposure session by up to several tenths of degrees. An accentuated change of the horizontal projection angle is particularly applicable at areas where the jaw is thin. In such a case the jointing of two subsequent exposure sequences is performed in an excellent manner.

In summary it can be stated that tho method in accordance with the invention achieves a continuous imaging of the dental arch and jaws offering a panoramic picture quality fully identical to that of a conventional panoramic radiographic image, yet allowing optimal selection of the projection orientation and distance of the X-ray beam for each imaged partial object, this being impossible in the conventional methods.

We claim:

1. A method of panoramic radiography for the dental arch and jaws, in which method by means of movable radiographing and/or imaging elements, several subsequent exposure sweep sequences are perform so that the an x-ray beam and an exposure movement of the movable elements are switched off for a preceding sequence, the movable elements are transferred to a new position and the exposure movement for a latter sequence is started and the x-ray beam is switched on, characterized in that the transfer movement of the movable elements is complemented by a corrective movement so that a new start position of the latter sequence is situated earlier relative to the position corresponding to the actual switch-on position of the x-ray beam in the latter sequence and that the movable elements are brought into motion prior to the switch-on instant of the x-ray beam so that desired positions and speeds of those elements moving at the switch-on instant are attained.

2. A method as claimed in claim 1, characterized in that the corrective movement is performed according to the following equation:

$$DP(i) = [VE(i) + VV(i)] \cdot \frac{TA}{2} + VV(i) \cdot TB + [VV(i) + VJ(i)] \cdot \frac{TC}{2}$$

where
- $DP(i)$ = added corrective translation in length units,
- $VE(i)$ = end velocity of exposure movement in the preceding sequence
- $VV(i)$ = velocity of transfer movement,
- $TA$ = inertial delay in the preceding sequence, i.e., time required for velocity change from $VE(i)$ to $VV(i)$,
- $TB$ = duration of corrective translation,
- $VJ(i)$ = desired velocity in the latter sequence,
- $TC$ = time required for velocity change from $VV(i)$ to $VJ(i)$.

3. A method in accordance with claim 1, characterized in that the corrective movement is performed so as to make the orientation of the X-ray beam at the start of the latter exposure sequence coincide with the orientation of the X-ray beam at the end of the preceding exposure sequence.

4. A method in accordance with claim 1, characterized in that the movable elements used in the radiography incorporate at least an X-ray source, a recording element for X-rays, an element for a rotational movement of the X-ray source and the recording element about the object to be radiographed placed between them such as a support arm together with the X-ray source and the recording elements at the opposite ends of the arm, and preferably an element capable of transferring and/or inclining the center of rotation of said rotational movement.

5. The method according to claim 1, wherein the switch-on instant of the x-ray beam for a latter sequence is chosen so that the position of the movable elements is exactly the means as at the switch-off instant for the immediately preceding sequence.

6. The method according to claim 1, wherein the movable elements include a rotatable arm a carrying an x-ray source at one end and a movable x-ray film at the opposite end, the radiography is carries our in four exposure sequences, covering in succession a first remote side area of the dental arch, a first frontal side area, an opposite second frontal side area, and, finally, an opposite second remote side area of the dental arch, whereby, at the transition between said first remove side area and said first frontal side area, and between the opposite second frontal side area and the second remote side area, respectively, the rotation center of said arm is displaced but the direction of the x-ray beam is maintained unchanged, and at the transition area between said first and second frontal side areas, the rotation center of said arm is displaced transversal and symmetrically in view of the axis of symmetry of the dental arch, the direction of the x-ray beam changing simultaneously by an angle of 10 to 30 degrees for the bypass of the cervical spine.

7. The method according to claim 6, wherein the direction of the x-ray beam is changed by an angle of about 20 degrees.

* * * * *